US005855918A

United States Patent [19]
Mrsny et al.

[11] Patent Number: 5,855,918
[45] Date of Patent: Jan. 5, 1999

[54] CYSTIC FIBROSIS THERAPY

[75] Inventors: Randall J. Mrsny, Redwood City; Ben-Quan Shen, San Francisco; Jonathan H. Widdicombe, Lafayette, all of Calif.

[73] Assignees: Genentech, Inc., South San Francisco; Children's Hospital Medical Center of Northern California; Regents of the University of CA, both of Oakland, all of Calif.

[21] Appl. No.: 713,048

[22] Filed: Sep. 12, 1996

Related U.S. Application Data

[60] Provisional application Nos. 60/003,581 Sep. 12, 1995 and 60/010,509 Jan. 24, 1996.

[51] Int. Cl.$^6$ ...................................................... A61K 35/16
[52] U.S. Cl. ......................... 424/530; 424/531; 424/532; 514/2; 514/21
[58] Field of Search ........................ 514/2, 21; 424/530, 424/531, 532

[56] References Cited

U.S. PATENT DOCUMENTS

| | | | |
|---|---|---|---|
| 5,227,158 | 7/1993 | Jardieu et al. | 424/85.5 |
| 5,316,921 | 5/1994 | Godowski et al. | 435/69.4 |
| 5,328,837 | 7/1994 | Godowski et al. | 435/69.4 |

FOREIGN PATENT DOCUMENTS

| | | |
|---|---|---|
| WO 92/13097 | 8/1992 | WIPO . |
| WO 92/20792 | 11/1992 | WIPO . |
| WO 93/15754 | 8/1993 | WIPO . |
| WO 95/29694 | 9/1995 | WIPO . |

OTHER PUBLICATIONS

*Remington's Pharmaceutical Sciences*, Oslo et al., eds., 16th edition, Mack Publishing Co. (1980).
Asami et al., "Purification and Characterization of Hepatocyte Growth Factor from Injured Liver of Carbon Tetrachloride–Treated Rats" *J. Biochem.* 109:8–13 (1991).
Bottaro et al., "Identification of the Hepatocyte Growth Factor Receptor as the c–met Proto–Oncogene Product" *Science* 251:802–804 (Feb. 15, 1991).
Boucher et al., "Na$^+$ Transport in Cystic Fibrosis Respiratory Epithelia" *J. Clin. Invest.* 78:1245–1252 (1986).
Chan et al., "Identification of a Competitive HGF Antagonist Encoded by an Alternative Transcript" *Science* 254:1382–1385 (1991).
Chan et al., "Isoforms of Human HGF and Their Biological Activities" *Hepatocyte Growth Factor–Scatter Factor (HGF–SF) and the C–Met Receptor*, I.D. Goldberg and E.M. Rosen eds., Basel:Birkhauser Verlag pp. 67–79 (1993).
Clarke et al., "Defective Epithelial Chloride Transport in a Gene–Targeted Mouse Model of Cystic Fibrosis" *Science* 257:1125–1128 (1992).
Comoglio, "Structure, Biosynthesis and Biochemical Properties of the HGF Receptor in Normal and Malignant Cells" *Hepatocyte Growth Factor–Scatter Factor (HGF–SF) and the C–Met Receptor*, I.D. Goldberg and E.M. Rosen eds., Basel:Birkhauser Verlag pp. 131–165 (1993).
Crepaldi et al., "Targeting of the SF/HGF Receptor to the Basolateral Domain of Polarized Epithelial Cells" *The Journal of Cell Biology* 125(2):313–320 (1994).
Di Renzo et al., "Selective Expression of the Met/HGF Receptor in Human Central Nervous System Microglia" *Oncogene* 8:219–222 (1993).
Fuller et al., "Cloning of a Bovine Renal Epithelial Na$^+$ Channel Subunit" *Am. J. Physiol.* 269:C641–C654 (1995).
Furlong, "The Biology of Hepatocyte Growth Factor/Scatter Factor" *BioEssays* 14:613–617 (1992).
Giordano et al., "Transfer of Motogenic and Invasive Response to Scatter Factor/Hepatocyte Growth Factor by Transfection of Human met Protooncogene" *Proc. Natl. Acad. Sci. USA* 90:649–653 (Jan. 1993).
Gohda et al., "Purification and Partial Characterization of Hepatocyte Growth Factor from Plasma of a Patient with Fulminant Hepatic Failure" *J. Clin. Invest.* 81:414–419 (1988).
Han et al., "Characterization of the DNF15S2 Locus on Human Chromosome 3: Identification of a Gene Coding for Four Kringle Domains with Homology to Hepatocyte Growth Factor" *Biochemistry* 30:9768–9780 (1991).
Hartmann et al., "A Functional Domain in the Heavy Chain of Scatter Factor/Hepatocyte Growth Factor Binds the c–Met Receptor and Induces Cell Dissociation but Not Mitogenesis" *Proc. Natl. Acad. Sci. USA* 89:11574–11578 (Dec. 1992).
Igawa et al., "Hepatocyte Growth Factor is a Potent Mitogen for Cultured Rabbit Renal Tubular Epithelial Cells" *Biochem. & Biophys. Res. Comm.* 174(2):831–838 (Jan. 31, 1991).
Jetten et al., "Persistence of Abnormal Chloride Conductance Regulation in Transformed Cystic Fibrosis Epithelia" *Science* 244:1472–1475 (1989).
Jiang et al., "Altered Fluid Transport Across Airway Epithelium in Cystic Fibrosis" *Science* 262:424–427 (1993).
Knowles et al., "Activation by Extracellular Nucleotides of Chloride Secretion in the Airway Epithelia of Patients with Cystic Fibrosis" *New England J. of Medicine* 325:533–538 (1991).
Lindroos et al., "Hepatocyte Growth Factor (Hepatopoietin A) Rapidly Increases in Plasma before DNA Synthesis and Liver Regeneration Stimulated by Partial Hepatectomy and Carbon Tetrachloride Administration" *Hepatology* 13(4):743–750 (1991).

(List continued on next page.)

*Primary Examiner*—Jean C. Witz
*Attorney, Agent, or Firm*—Diane L. Marschang

[57] ABSTRACT

The invention provides methods for treating cystic fibrosis and other pathological conditions in mammals using hepatocyte growth factor ("HGF"). The invention also provides articles of manufacture and kits containing HGF.

7 Claims, 9 Drawing Sheets

OTHER PUBLICATIONS

Lokker and Godowski, "Generation and Characterization of a Competitive Antagonist of Human Hepatocyte Growth Factor, HGF/NK1" *Journal of Biological Chemistry* 268:17145–17150 (1993).

Lokker et al., "Structure–Function Analysis of Hepatocyte Growth Factor: Identification of Variants that Lack Mitogenic Activity Yet Retain High Affinity Receptor Binding" *EMBO Journal* 11(7):2503–2510 (1992).

Matsumoto et al., "Deletion of Kringle Domains or the N–Terminal Hairpin Structure in Hepatocyte Growth Factor Results in Marked Decreases in Related Biological Activities" *Biochem. & Biophys. Res. Comm.* 181(2):691–699 (Dec. 16, 1991).

Matsumoto et al., "Hepatocyte Growth Factor is a Potent Stimulator of Human Melanocyte DNA Synthesis and Growth" *Biochem. & Biophys. Res. Comm.* 176(1):45–51 (Apr. 15, 1991).

McDonald et al., "Liddle's Syndrome Mutations Increase Activity of the Epithelial $Na^+$ Channel" *American Society Cell Biology* (1995).

Michalopoulos et al., "Control of Hepatocyte Replication by Two Serum Factors" *Cancer Research* 44:4414–4419 (Oct. 1984).

Miyazawa et al., "An Alternatively Processed mRNA Generated from Human Hepatocyte Growt Factor Gene" *European Journal of Biochemistry* 197:15–22 (1991).

Miyazawa et al., "Molecular Cloning and Sequence Analysis of cDNA for Human Hepatocyte Growth Factor" *Biochem. & Biophys. Res. Comm.* 163(2):967–973 (Sep. 15, 1989).

Montesano et al., "Identification of a Fibroblast–Derived Epithelial Morphogen as Hepatocyte Growth Factor" *Cell* 67:901–908 (Nov. 29, 1991).

Naka et al., "Activation of Hepatocyte Growth Factor by Proteolytic Conversion of a Single Chain Form to a Heterodimer" *The Journal of Biological Chemistry* 267(28):20114–20119 (1992).

Nakamura et al., "Molecular Cloning and Expression of Human Hepatocyte Growth Factor" *Nature* 342:440–443 (Nov. 23, 1989).

Nakamura et al., "Partial Purification and Characterization of Hepatocyte Growth Factor from Serum of Hepatectomized Rats" *Biochem. & Biophys. Res. Comm.* 122:1450–1459 (Aug. 16, 1984).

Nakamura et al., "Purification and Characterization of a Growth Factor from Rat Platelets for Mature Parenchymal Hepatocytes in Primary Cultures" *Proc. Natl. Acad. Sci. USA* 83:6489–6493 (1986).

Nakamura et al., "Purification and Subunit Structure of Hepatocyte Growth Factor from Rat Platelets" *FEBS Letters* 224(2):311–316 (Nov. 1987).

Naldini et al., "Hepatocyte Growth Factor (HGF) Stimulates the Tyrosine Kinase Activity of the Receptor Encoded by the Proto–Oncogene c–MET" *Oncogene* 6:501–504 (1991).

Naldini et al., "Scatter Factor and Hepatocyte Growth Factor are Indistinguishable Ligands for the MET Receptor" *EMBO Journal* 10(10):2867–2878 (1991).

Okajima et al., "Primary Structure of Rat Hepatocyte Growth Factor and Induction of Its mRNA During Liver Regeneration Following Hepatic Injury" *European Journal of Biochemistry* 193:375–381 (1990).

Panos et al., "Keratinocyte Growth Factor and Hepatocyte Growth Factor/Scatter Factor are Heparin–binding Growth Factors for Alveolar Type II Cells in Fibroblast–conditioned Medium" *J. Clin. Investigation* 92:969–977 (1993).

Park et al., "Sequence of MET Protooncogene cDNA has Features Characteristic of the Tyrosine Kinase Family of Growth–Factor Receptors" *Proc. Natl. Acad. Sci. USA* 84:6379–6383 (1987).

Ponzetto et al., "c–met is Amplified But Not Mutated in a Cell Line with an Activated met Tyrosine Kinase" *Oncogene* 6:553–559 (1991).

Prat et al., "C–Terminal Truncated Forms of Met, the Hepatocyte Growth Factor Receptor" *Molecular & Cellular Biology* 11(12):5954–5962 (1991).

Rodrigues et al., "Alternative Splicing Generates Isoforms of the met Receptor Tyrosine Kinase Which Undergo Differential Processing" *Molecular & Cellular Biology* 11(6):2962–2970 (1991).

Roos et al., "Induction of Liver Growth in Normal Mice by Infusion of Hepatocyte Growth Factor/Scatter Factor" *Am. J. Physiol.* 268:G380–G386 (1995).

Rubin et al., "A Broad–Spectrum Human Lung Fibroblast–Derived Mitogen is a Variant of Hepatocyte Growth Factor" *Proc. Natl. Acad. Sci. USA* 88:415–419 (1991).

Russell et al., "Partial Characterization of a Hepatocyte Growth Factor From Rat Platelets" *J. Cellular Physiology* 119:183–192 (1984).

Seki et al., "Isolation and Expression of cDNA for Different Forms of Hepatocyte Growth Factor from Human Leukocyte" *Biochem. and Biophys. Res. Commun.* 172(1):321–327 (Oct. 15, 1990).

Shen et al., "Calu–3: a Human Airway Epithelial Cell Line that Shows cAMP–dependent Cl– Secretion" *Amer. J. Physiol.* 266(5, part 1):L493–L501 (1994).

Shen et al., "Hepatocyte Growth Factor Increases Differentiation of Human Tracheal Epithelial Cell Cultures" *Pediatric Pulmonology—Ninth Annual North American Cystic Fibrosis Conference* (Poster Session Abstract No. 222) Supplement 12:241–242 (Sep. 1995).

Shen et al., "Role of CFTR in Chloride Secretion Across Human Tracheal Epithelium" *Am. J. Phys.* 269:L561–L566 (1995).

Singh–Kaw et al., "Stimulatory Effects of Hepatocyte Growth Factor on Normal and Neoplastic Human Bronchial Epithelial Cells" *Am. J. Physiology* 268(6, part 1):L1012–L1020 (1995).

Smith et al., "Fluid and Electrolyte Transport by Cultured Human Airway Epithelia" *J. Clin. Invest.* 91:1590–1597 (1993).

Snyder et al., "Mechanism by Which Liddle's Syndrome Mutations Increase Activity of a Human Epithelial Na+ Channel" *Cell* 83:969–978 (1995).

Sorscher et al., "Antibodies Against Purified Epithelial Sodium Channel Protein from Bovine Renal Papilla" *Am. J. Physiol.* 255:C835–C843 (1988).

Stoker et al., "Scatter Factor is a Fibroblast–Derived Modulator of Epithelial Cell Mobility" *Nature* 327:239–242 (May 21, 1987).

Stutts et al., "CFTR as a cAMP–Dependent Regulator of Sodium Channels" *Science* 269:847–850 (1995).

Tashiro et al., "Deduced Primary Structure of Rat Hepatocyte Growth Factor and Expression of the mRNA in Rat Tissues" *Proc. Natl. Acad. Sci. USA* 87:3200–3204 (1990).

Ussing et al., "Active Transport of Sodium as the Source of Electric Current in the Short–circuited Isolated Frog Skin" *Acta Phys. Scandinav.* 23:110–127 (1951).

Weidner et al., "Scatter Factor: Molecular Characteristics and Effect on the Invasiveness of Epithelial Cells" *Journal of Cell Biology* 111:2097–2108 (Nov. 1990).

Welsh et al., "Cystic Fibrosis" *J. Clin. Invest.* 80:1523–1526 (Dec. 1987).

Widdicombe, "Electrical Methods for Studying Ion and Fluid Transport Across Airway Epithelia" *Methods in Bronchial Mucology*, Braga et al., eds. pp. 335–345 (1988).

Zarnegar et al., "The Many Faces of Hepatocyte Growth Factor: from Hepatopoiesis to Hematopoiesis" *Journal of Cell Biology* 129:1177–1180 (1995).

Fujita et al., "Hepatocyte Growth Factor and Idiopathic Pulmonary Fibrosis" *Chest* 109(5):1413 (1996).

Matsuda et al., "Hepatocyte Growth Factor Supresses the Onset of Liver Cirrhosis and Abrogates Lethal Hepatic Dysfunction in Rats" *J. of Biochemistry* 118(3):643–649 (1995).

CYSTIC FIBROSIS THERAPY

REFERENCE TO GOVERNMENT RIGHTS

This invention was made with Government support under Grant No. P50 HL42368 awarded by the Department of Health and Human Services, National Heart, Lung, and Blood Institute. The Government has certain rights to this invention.

RELATED APPLICATIONS

This application is a non-provisional application filed under 37 CFR 1.53(b) (1) and 35 USC 111(a), claiming priority under 35 USC 119(e) to provisional application number 60/003,581 filed Sep. 12, 1995 and to provisional application number 60/010,509 filed Jan. 24, 1996, the contents of which are incorporated herein by reference.

FIELD OF THE INVENTION

The invention relates generally to methods and compositions which can be employed in treating mammals having pulmonary or respiratory disease, including cystic fibrosis. The invention also relates generally to methods and compositions which can be employed in treating mammals having pathological conditions associated with increased $Na^+$ and fluid absorption by cells.

BACKGROUND OF THE INVENTION

Various pulmonary and respiratory diseases, such as pneumonia, bronchitis, and cystic fibrosis, are often accompanied by viscous secretions in respiratory airways of the patient. Obstruction of the airways by such secretions can cause respiratory distress, and in some cases, can lead to respiratory failure and death.

Investigators have compared the $Na^+$ and $Cl^-$ permeability of normal epithelia and epithelia in patients suffering from such diseases described above. [See, e.g., Welsh et al., *J. Clin. Invest.*, 80:1523–1526 (1987)]. Measurements of short-circuit current ("$I_{sc}$") have shown that normal human airway epithelia are predominantly $Na^+$ absorbing under baseline conditions while $Cl^-$ secretion is relatively small or absent [Smith et al., *J. Clin. Invest.*, 91:1590–1597 (1993)]. Baseline $Na^+$ absorption, however, is elevated approximately two-fold in cystic fibrosis ("CF") patients [Boucher et al., *J. Clin. Invest.*, 78:1245–1252 (1986)].

Recently, a cAMP-dependent $Cl^-$ channel has been identified to be defective in CF patients. This channel, referred to as CF transmembrane regulator ("CFTR"), has been suggested to play an important role in normal $Na^+$ transport [Stutts et al., *Science*, 269:847–850 (1995)]. Despite the presence of several $Cl^-$ channels being present in the apical membrane of airway epithelial cells, it is believed that the CFTR provides the major $Cl^-$ conductance pathway in these cells and that this channel is close to maximally activated under baseline conditions [Shen et al., *Am. J. Phys.*, 269:L561–L566 (1995)]. In the absence of significant $Cl^-$ efflux, the increased basal $Na^+$ influx (and associated fluid absorption) observed in CF airway epithelia has been suggested to contribute to the formation of the abnormally hydrated, viscous mucous secretions which occlude the airways in CF disease [Jiang et al., *Science*, 262:424–427 (1993)].

Certain pharmacological approaches to rectify the abnormal fluid absorption in CF patients have been described. For instance, some investigators have described stimulating epithelial $Cl^-$ secretion using agents such as uracil 5' triphosphate ("UTP") to raise intracellular calcium ion levels and attenuate $Ca^{2+}$ activated $Cl^-$ channels [Knowles et al., *N. Engl. J. Med.*, 325:533–538 (1991)]. Another approach has been to use aerosolized amiloride to block $Na^+$ absorption [Boucher et al., supra]. The present invention is directed to the use of hepatocyte growth factor ("HGF") to modulate fluid absorption by modulating the expression of $Na^+$ channels. As described below, the present inventors have surprisingly discovered that HGF produces an effective and prolonged block of amiloride-sensitive $Na^+$ absorption.

It is recognized in the art that HGF functions as a growth factor for particular tissues and cell types. HGF was identified initially as a mitogen for hepatocytes [Michalopoulos et: al., *Cancer Res.*, 44:4414–4419 (1984); Russel et al., *J. Cell. Physiol.*, 119:183–192 (1984); Nakamura et al., *Biochem. Biophys. Res. Comm.*, 122:1450–1459 (1984)]. Nakamura et al., supra, reported the purification of HGF from the serum of partially hepatectomized rats. Subsequently, HGF was purified from rat platelets, and its subunit structure was determined [Nakamura et al., *Proc. Natl. Acad. Sci. USA*, 83:6489–6493 (1986); Nakamura et al., *FEBS Letters*, 224:311–316 (1987)]. The purification of human HGF ("huHGF") from human plasma was first described by Gohda et al., *J. Clin. Invest.*, 81:414–419 (1988).

Both rat HGF and huHGF have been molecularly cloned, including the cloning and sequencing of a naturally occurring variant lacking 5 amino acids designated "delta5 HGF" [Miyazawa et al., *Biochem. Biophys. Res. Comm.*, 163:967–973 (1989); Nakamura et al., *Nature*, 342:440–443 (1989); Seki et al, *Biochem. Biophys. Res. Commun.*, 172:321–327 (1990); Tashiro et al., *Proc. Natl. Acad. Sci. USA*, 87:3200–3204 (1990); Okajima et al., *Eur. J. Biochem.*, 193:375–381 (1990)].

The mature form of huHGF, corresponding to the major form purified from human serum, is a disulfide linked heterodimer derived by proteolytic cleavage of the human pro-hormone between amino acids R494 and V495. This cleavage process generates a molecule composed of an α-subunit of 440 amino acids ($M_r$ 69 kDa) and a β-subunit of 234 amino acids ($M_r$ 34 kDa). The nucleotide sequence of the huHGF cDNA reveals that both the α- and the β-chains are contained in a single open reading frame coding for a pre-pro precursor protein. In the predicted primary structure of mature huHGF, an interchain S-S bridge is formed between Cys 487 of the α-chain and Cys 604 in the β-chain [see Nakamura et al., *Nature*, supra]. The N-terminus of the α-chain is preceded by 54 amino acids, starting with a methionine group. This segment includes a characteristic hydrophobic leader (signal) sequence of 31 residues and the prosequence. The α-chain starts at amino acid (aa) 55, and contains four kringle domains. The kringle 1 domain extends from about aa 128 to about aa 206, the kringle 2 domain is between about aa 211 and about aa 288, the kringle 3 domain is defined as extending from about aa 303 to about aa 383, and the kringle 4 domain extends from about aa 391 to about aa 464 of the α-chain.

The definition of the various kringle domains is based on their homology with kringle-like domains of other proteins (such as prothrombin and plasminogen), therefore, the above limits are only approximate. To date, the function of these kringles has not been determined. The β-chain of huHGF shows high homology to the catalytic domain of serine proteases (38% homology to the plasminogen serine protease domain). However, two of the three residues which form the catalytic triad of serine proteases are not conserved in huHGF. Therefore, despite its serine protease-like domain, huHGF appears to have no proteolytic activity, and the precise role of the β-chain remains unknown. HGF contains four putative glycosylation sites, which are located at positions 294 and 402 of the α-chain and at positions 566 and 653 of the β-chain.

In a portion of cDNA isolated from human leukocytes, in-frame deletion of 15 base pairs was observed. Transient expression of the cDNA sequence in COS-1 cells revealed that the encoded HGF molecule (delta5 HGF) lacking 5 amino acids in the kringle 1 domain was fully functional [Seki et al., supra].

A naturally occurring huHGF variant has been identified which corresponds to an alternative spliced form of the huHGF transcript containing the coding sequences for the N-terminal finger and first two kringle domains of mature huHGF [Chan et al., Science, 254:1382–1385 (1991); Miyazawa et al., Eur. J. Biochem., 197:15–22 (1991)]. This variant, designated HGF/NK2, has been proposed to be a competitive antagonist of mature huHGF.

Comparisons of the amino acid sequence of rat HGF with that of huHGF have revealed that the two sequences are highly conserved and have the same characteristic structural features. The length of the four kringle domains in rat HGF is exactly the same as in huHGF. Furthermore, the cysteine residues are located in exactly the same positions, an indication of similar three-dimensional structures [Okajima et al., supra; Tashiro et al., supra].

HGF and HGF variants are described further in U.S. Pat. Nos. 5,227,158; 5,316,921; and 5,328,837.

The HGF receptor has been identified as the product of the c-Met proto-oncogene [Bottaro et al., Science, 251:802–804 (1991); Naldini et al., Oncogene, 6:501–504 (1991); WO 92/13097 published Aug. 6, 1992; WO 93/15754 published Aug. 19, 1993]. The receptor is usually referred to as "c-Met" or "p190$^{MET}$" and typically comprises, in its native form, a 190-kDa heterodimeric (a disulfide-linked 50-kDa α-chain and a 145-kDa β-chain) membrane-spanning tyrosine kinase protein [Park et al., Proc. Natl. Acad. Sci. USA, 84:6379–6383 (1987)]. Several truncated forms of the c-Met receptor have also been described [WO 92/20792; Prat et al., Mol. Cell. Biol., 11:5954–5962 (1991)].

The binding activity of HGF to its receptor is believed to be conveyed by a functional domain located in the N-terminal portion of the HGF molecule, including the first two kringles [Matsumoto et al., Biochem. Biophys. Res. Commun., 181:691–699 (1991); Hartmann et al., Proc. Natl. Acad. Sci., 89:11574–11578 (1992); Lokker et al., EMBO J., 11:2503–2510 (1992); Lokker and Godowski, J. Biol. Chem., 268:17145–17150 (1993)]. The c-Met protein becomes phosphorylated on tyrosine residues of the 145-kDa β-subunit upon HGF binding.

Various biological activities have been described for HGF and its receptor [see, generally, Chan et al., Hepatocyte Growth Factor—Scatter Factor (HGF-SF) and the C-Met Receptor, Goldberg and Rosen, eds., Birkhauser Verlag-Basel (1993), pp. 67–79]. It has been observed that levels of HGF increase in the plasma of patients with hepatic failure [Gohda et al., supra] and in the plasma [Lindroos et al., Hepatol., 13:743–750 (1991)] or serum [Asami et al., J. Biochem., 109:8–13 (1991)] of animals with experimentally induced liver damage. The kinetics of this response are usually rapid, and precedes the first round of DNA synthesis during liver regeneration. HGF has also been shown to be a mitogen for certain cell types, including melanocytes, renal tubular cells, keratinocytes, certain endothelial cells and cells of epithelial origin [Matsumoto et al., Biochem. Biophys. Res. Commun., 176:45–51 (1991); Igawa et al., Biochem. Biophys. Res. Commun., 174:831–838 (1991); Han et al., Biochem., 30:9768–9780 (1991); Rubin et al., Proc. Natl. Acad. Sci. USA, 88:415–419 (1991)]. Both HGF and the c-Met protooncogene have been postulated to play a role in microglial reactions to CNS injuries [DiRenzo et al., Oncogene, 8:219–222 (1993)].

HGF can also act as a "scatter factor", an activity that promotes the dissociation of epithelial and vascular endothelial cells in vitro [Stoker et al., Nature, 327:239–242 (1987); Weidner et al., J. Cell Biol., 111:2097–2108 (1990); Naldini et al., EMBO J., 10:2867–2878 (1991); Giordano et al., Proc. Natl. Acad. Sci. USA, 90:649–653 (1993)]. Moreover, HGF has recently been described as an epithelial morphogen [Montesano et al., Cell, 67:901–908 (1991)]. Therefore, HGF has been postulated to be important in tumor invasion [Comoglio, Hepatocyte Growth Factor—Scatter Factor (HGF-SF) and the C-Met Receptor, Goldberg and Rosen, eds., Birkhauser Verlag-Basel (1993), pp. 131–165].

SUMMARY OF THE INVENTION

The invention provides methods for treating cystic fibrosis comprising administering to a mammal diagnosed as having cystic fibrosis an effective amount of HGF. The HGF alone may be administered to the mammal, or alternatively, may be administered to the mammal in combination with other therapies and/or pharmacologic agents, such as described herein.

The invention also provides methods for reducing sodium ion absorption in mammalian cells, comprising exposing said cells to an effective amount of HGF.

The invention further provides articles of manufacture and kits which contain HGF.

Although not being bound by any particular theory, it is presently believed that the HGF can be used to substantially diminish abnormally high amiloride-sensitive Na$^+$ and fluid absorption by cells, thereby treating pathologic conditions associated with diseases such as cystic fibrosis. The HGF may also be used to re-establish the epithelia lining damaged passageways by proliferation of epithelial cells.

DETAILED DESCRIPTION OF THE INVENTION

I. Definitions

Figure 1:
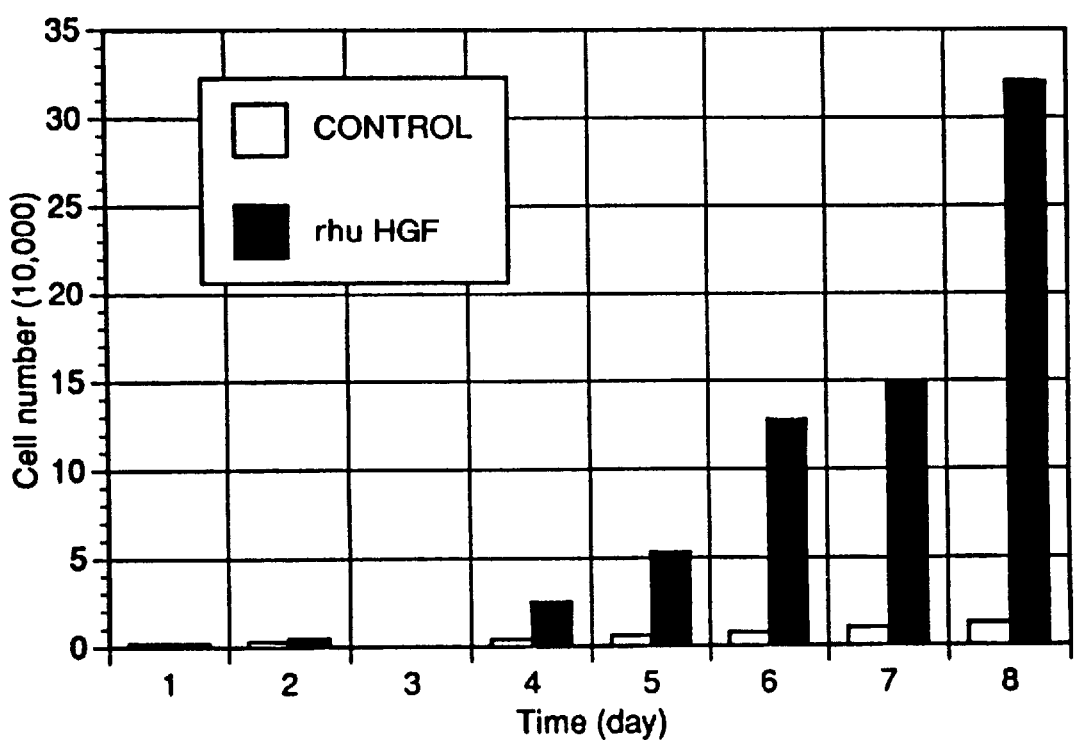
FIG. 1 includes a bar diagram showing the effect of rhuHGF on proliferation of normal human tracheal cells in vitro.

As used herein, the terms "hepatocyte growth factor" and "HGF" refer to a growth factor typically having a structure with six domains (finger, Kringle 1, Kringle 2, Kringle 3, Kringle 4 and serine protease domains). Fragments of HGF constitute HGF with fewer domains and variants of HGF may have some of the domains of HGF repeated; both are included if they still retain their respective ability to bind an HGF receptor. The terms "hepatocyte growth factor" and "HGF" include hepatocyte growth factor from humans ("huHGF") and any non-human mammalian species, and in particular rat HGF. The terms as used herein include mature, pre, pre-pro, and pro forms, purified from a natural source, chemically synthesized or recombinantly produced. Human HGF is encoded by the cDNA sequence published by Miyazawa et al., 1989, supra, or Nakamura et al., 1989, supra. The sequences reported by Miyazawa et al. and Nakamura et al. differ in 14 amino acids. The reason for the differences is not entirely clear; polymorphism or cloning artifacts are among the possibilities. Both sequences are specifically encompassed by the foregoing terms. It will be understood that natural allelic variations exist and can occur among individuals, as demonstrated by one or more amino acid differences in the amino acid sequence of each individual. The HGF of the invention preferably has at least about 80% sequence identity, more preferably at least about 90% sequence identity, and even more preferably, at least about 95% sequence identity with a native mammalian HGF. The terms "hepatocyte growth factor" and "HGF" specifically include the delta5 huHGF as disclosed by Seki et al., supra.

The terms "HGF receptor" and "c-Met" when used herein refer to a cellular receptor for HGF, which typically includes an extracellular domain, a transmembrane domain and an intracellular domain, as well as variants and fragments thereof which retain the ability to bind HGF. The terms "HGF receptor" and "c-Met" include the polypeptide molecule that comprises the full-length, native amino acid sequence encoded by the gene variously known as $p190^{MET}$. The present definition specifically encompasses soluble forms of HGF receptor, and HGF receptor from natural sources, synthetically produced in vitro or obtained by genetic manipulation including methods of recombinant DNA technology. The HGF receptor variants or fragments preferably share at least about 65% sequence homology, and more preferably at least about 75% sequence homology with any domain of the human c-Met amino acid sequence published in Rodrigues et al., *Mol. Cell. Biol.*, 11:2962–2970 (1991); Park et al., *Proc. Natl. Acad. Sci.*, 84:6379–6383 (1987); or Ponzetto et al., *Oncogene*, 6:553–559 (1991).

The term "cystic fibrosis" when used herein refers to or describes the physiological condition in mammals typically characterized by viscous or mucus secretions that tend to obstruct or occlude various internal passageways in a mammal, including but not limited to, pancreatic ducts, bile ducts, and respiratory airways.

The terms "treating," "treatment," and "therapy" as used herein refer to curative therapy, prophylactic therapy, and preventative therapy.

The term "mammal" as used herein refers to any animal classified as a mammal, including humans, cows, horses, dogs and cats. In a preferred embodiment of the invention, the mammal is a human.

II. Compositions and Methods of the Invention

The present invention provides methods for treating cystic fibrosis using hepatocyte growth factor, referred to hereinafter as "HGF". It is also contemplated that HGF will be particularly useful for the treatment of mammals having a pathological condition which is accompanied by abnormal, viscous or inspissated mucus secretions and/or resulting from increased $Na^+$ or fluid absorption by cells. Examples of such conditions include acute or chronic bronchopulmonary disease (infectious pneumonia, bronchitis or tracheobronchitis, bronchiectasis, asthma, TB or fungal infections), atelectasis due to tracheal or bronchial impaction, complications of tracheostomy, and Liddle's Syndrome.

The HGF useful in the practice of the present invention can be prepared in a number of ways. For instance, the HGF can be prepared using an isolated or purified form of HGF. Methods of isolating and purifying HGF from natural sources are known in the art. Such isolation and purification methods can be employed for obtaining HGF from serum or plasma. Alternatively, HGF can be chemically synthesized and prepared using recombinant DNA techniques known in the art and described in further detail in Example 1 below.

The HGF may be from human or any non-human species. For instance, a mammal may have administered HGF from a different mammalian species (e.g., rats can be treated with human HGF). Preferably, however, the mammal is treated with homologous HGF (e.g., humans are treated with human HGF) to avoid potential immune reactions to the HGF.

In a preferred embodiment of the invention, methods for treating cystic fibrosis are provided. In the methods, HGF is administered to a mammal diagnosed as having cystic fibrosis. It is of course contemplated that the methods of the invention can be employed in combination with still other therapeutic techniques such as percussion physical therapy, enzyme replacement therapy (such as pancreatic enzymes), and transplant therapy.

The HGF is preferably administered to the mammal in a pharmaceutically-acceptable carrier. Suitable carriers and their formulations are described in *Remington's Pharmaceutical Sciences*, 16th ed., 1980, Mack Publishing Co., edited by Oslo et al. Typically, an appropriate amount of a pharmaceutically-acceptable salt is used in the formulation to render the formulation isotonic. Examples of the pharmaceutically-acceptable carrier include liquids such as saline, Ringer's solution and dextrose solution. The pH of the solution is preferably from about 5 to about 8, and more preferably from about 7 to about 7.5. The formulation may also comprise a lyophilized powder. Further carriers include sustained release preparations such as semipermeable matrices of solid hydrophobic polymers, which matrices are in the form of shaped articles, e.g., films, liposomes or microparticles. It will be apparent to those persons skilled in the art that certain carriers may be more preferable depending upon, for instance, the route of administration and concentration of HGF being administered.

The HGF can be administered to the mammal by injection (e.g. intravenous, intraperitoneal, subcutaneous, intramuscular), or by other methods such as infusion that ensure its delivery to the bloodstream in an effective form. Commercially available nebulizers for liquid formulations, including jet nebulizers and ultrasonic nebulizers may also be useful for administration. Liquid formulations may be directly nebulized and lyophilized power nebulized after reconstitution. Alternatively, HGF may be aerosolized using a metered dose inhaler, or inhaled as a lyophilized and milled powder. In addition, the liquid formulation of HGF may be directly instilled in the nasotracheal or endotracheal tubes in intubated patients.

Effective dosages and schedules for administering the HGF may be determined empirically, and making such determinations is within the skill in the art. Those skilled in the art will understand that the dosage of HGF that must be administered will vary depending on, for example, the mammal which will receive the HGF, the route of administration, the particular type of HGF used and other drugs being administered to the mammal. A typical daily dosage of the HGF used alone might range from about 1 $\mu$g/kg to up to 100 mg/kg of body weight or more per day, depending on the factors mentioned above.

HGF may also be administered along with other pharmacologic agents used to treat the conditions listed above, such as UTP, amiloride, DNase, antibiotics, bronchodilators, anti-inflammatory agents, and mucolytics (e.g. n-acetyl-cysteine). It may also be useful to administer HGF along with other therapeutic human proteins such as protease inhibitors, gamma-interferon, enkephalinase, lung surfactant, and colony stimulating factors. The HGF may be administered sequentially or concurrently with the one or more other pharmacologic agents. The amounts of HGF and pharmacologic agent depend, for example, on what type of drugs are used, the disease being treated, and the scheduling and routes of administration.

Following administration of HGF to the mammal, the mammal's physiological condition can be monitored in various ways well known to the skilled practitioner.

In another embodiment of the invention, there are provided articles of manufacture and kits containing materials useful for treating the pathological conditions described herein, including cystic fibrosis. The article of manufacture comprises a container with a label. Suitable containers include, for example, bottles, vials, and test tubes. The containers may be formed from a variety of materials such as glass or plastic. The container holds a composition having an active agent which is effective for treating, for example, cystic fibrosis. The active agent in the composition is HGF. The label on the container indicates that the composition is used for treating, for example, cystic fibrosis, and may also indicate directions for in vivo use, such as those described above.

The kit of the invention comprises the container described above and a second container comprising a pharmaceutically-acceptable carrier or buffer. It may further include other materials desirable from a commercial and user standpoint, including other buffers, diluents, filters, needles, syringes, and package inserts with instructions for use.

The invention will be more fully understood by reference to the following examples. They should not, however, be construed as limiting the scope of the invention. All reference citations herein are incorporated by reference.

EXAMPLES

Example 1

Recombinant human HGF ("rhuHGF") was produced in CHO cells using a procedure modified from Naka et al., *J.*

*Biol. Chem.*, 267:20114–20119 (1992). rhuHGF-transfected cells were grown in a 400 L bioreactor in medium containing 2% fetal bovine serum for 8 days. Culture supernatant containing rhuHGF was concentrated and clarified, then conditioned by the addition of solid NaCl to 0.3M. rhuHGF was then purified in a single step using cation exchange chromatography. Conditioned, concentrated culture supernatant was loaded onto a column of S-Sepharose™ Fast Flow equilibrated in 20 mM Tris, pH 7.5, 0.3M NaCl. After washing out unbound protein, rhuHGF was eluted in a linear gradient from 20 mM Tris, pH 7.5, 0.3M NaCl to 20 mM Tris, pH 7.5, 1.2M NaCl. rhuHGF-containing fractions were pooled based on SDS-PAGE analysis. The S-Sepharose™ Fast Flow pool was concentrated and exchanged into 20 mM Tris, pH 7.5, 0.5M NaCl by gel filtration on Sephadex G25 to a final concentration of about 3–5 mg/ml. A rhuHGF stock solution was then prepared by diluting the rhuHGF in assay buffer (0.5% bovine serum albumin, 0.05% Tween-20, 0.01% Thimersol in PBS) to a concentration of 10 $\mu$g/ml.

Proliferation of primary isolates of autopsied, normal human tracheal epithelial cells (obtained from University of California, San Francisco Medical Center) was measured by monitoring the growth rate of the cells plated at low density (approximately 2000 cells/cm$^2$) on transparent, permeable filters. rhuHGF (at concentrations of greater than 50 ng/ml) markedly increased the cell number and scattering activity after 2–3 days when added at the time of seeding the cells. (See FIG. 1). A correlation between rhuHGF concentration and augmented growth rate was also observed.

Differentiation of the cultured tracheal cells was also measured by $I_{sc}$ current. The tracheal cells were placed onto Nucleopore cell culture inserts (0.45 micron pore size, 1 cm$^2$ surface area) coated with human placental collagen, and cultured in 2% USG medium as described in Shen et al., *Am. J. Phys.*, 266:L493–L501 (1994). The cells were treated with 50 ng/ml—1 $\mu$g/ml rhuHGF basolaterally 8–14 days after plating, a point when the cell monolayers had transepithelial resistance ($R_{te}$)>50 ohm/cm$^2$ as determined using a "chop-stick" voltmeter (Millicell®-ERS, Millipore, Bedford, Mass.). After 24–48 hours following addition of the rhuHGF, ion transport activities were measured in Ussing chambers using standard methods Ussing et al., *Acta Phys. Scandinav.*, 23:110–127 (1951); Widdicombe, *Methods in Bronchial Mucology*, Braga et al., eds., pp. 335–345 (1988).

Confluent cell sheets were cut out from the filter inserts, and mounted between Lucite half chambers. Transepithelial potential difference was clamped to zero by an external current passing circuit, and the resulting $I_{sc}$ was recorded continuously on a chart recorder. $R_{te}$ was determined from the current pulses needed to clamp the voltage to 0.5 or 1.0 mV for 20 msec every 20 sec. Warm, oxygenated Krebs-Henseleit solution was circulated across both faces of the filters by gas-lift oxygenators. The cells were then challenged with apical additions of 10 $\mu$M isoproterenol ("Iso"), 10 $\mu$M histamine ("His"), 10 $\mu$M methacholine ("Mch") or 1 $\mu$M bradykinin ("BK").

Figure 2A:
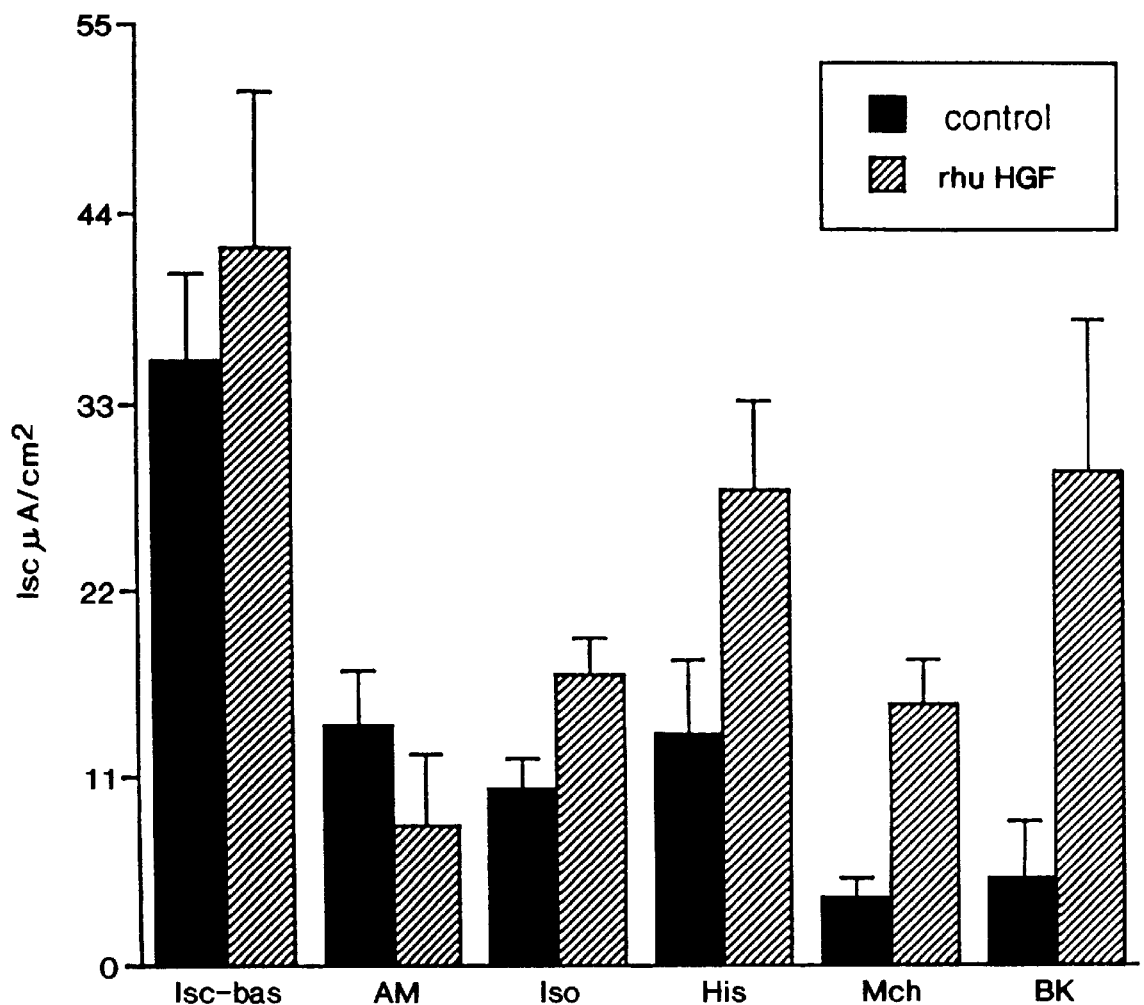
FIG. 2A includes a bar diagram comparing the response of normal human tracheal cells to challenge with amiloride, isoproterenol, histamine, methacholine and bradykinin following exposure to 100 ng/ml rhuHGF in vitro.

The results are shown in FIG. 2A for control cells (receiving no rhuHGF treatment) and for tracheal cells treated with 100 ng/ml rhuHGF. The measured baseline $I_{sc}$ is reported as "Isc-bas". Treatment with rhuHGF enhanced differentiation of the tracheal cells as reflected by the increase in $I_{sc}$, which reading was indicative of an increased responsiveness to challenge with Cl$^-$ secretogogues.

Example 2

JME/CF 15 cells were cultured, and $R_{te}$ and $I_{sc}$ were measured as described in Example 1. JME/CF 15 cells (obtained from D. Jefferson, New England Medical Center Hospitals, Inc., Boston, Mass.) is a cell line derived by SV40-transformation of primary cultures of nasal epithelium from a CF patient. The cell line demonstrates a CF phenotype characterized by a relatively high level of amiloride-sensitive $Na^+$ absorption and lack of cAMP-activated $Cl^-$ secretion in vitro.

The results are shown in Table 1. Changes in short-circuit currents ($\Delta I_{sc}$) following apical addition of $10^{-5}M$ amiloride (AM) and basolateral challenge with $10^{-5}M$ isoproterenol (ISO) are given as means±SE (n=6). Tests of statistical significance between means were performed with paired or unpaired Student's t-test. P<0.05 was regarded as significant.

Treatment of the cells with rhuHGF did not significantly affect monolayer resistance, while the baseline $I_{sc}$ was reduced, as shown in Table 1 below. The rhuHGF-treated cells showed marked decreases in baseline $I_{sc}$ and sensitivity to amiloride when compared on the same day with control cells. No affect on $Cl^-$ channel activity was observed, as evidenced by a lack of response to the challenges with isoproterenol, histamine, methacholine or bradykinin. Only a small effect was observed following ouabain addition suggesting that inhibition of $I_{sc}$ by amiloride was complete, and that amiloride-sensitive sodium absorption accounted for essentially all the $I_{sc}$. The effects of amiloride on $I_{sc}$ were not affected by pretreatment with $10^{-4}M$ bumetanide for 15 min. in the basolateral medium (data not shown), indicating that differences in sensitivity to amiloride between treated and untreated cells were not due to induction of $Cl^-$ secretion.

TABLE 1

| PARAMETER | CONTROL | 100 ng/ml rhuHGF |
|---|---|---|
| $R_{te}$ | 120 ± 14 $\Omega/cm^2$ | 106 ± 11 $\Omega/cm^2$ |
| Baseline $I_{sc}$ | 25.3 ± 1.6 $\mu A/cm^2$ | 2.1 ± 0.8 $\mu A/cm^2$* |
| $\Delta I_{sc}$ (AM) | 27.2 ± 2.0 $\mu A/cm^2$ | 4.5 ±0.8 $\mu A/cm^2$* |
| $\Delta I_{sc}$ (ISO) | 0 ± 0 $\mu A/cm^2$ | 0 ± 0 $\mu A/cm^2$ |

*significantly different from control value
For comparison, the baseline $I_{sc}$ values for CF and non-CF tracheal epithelium are approximately 30 and 10 $\mu A/cm^2$, respectively.

Figure 2B:
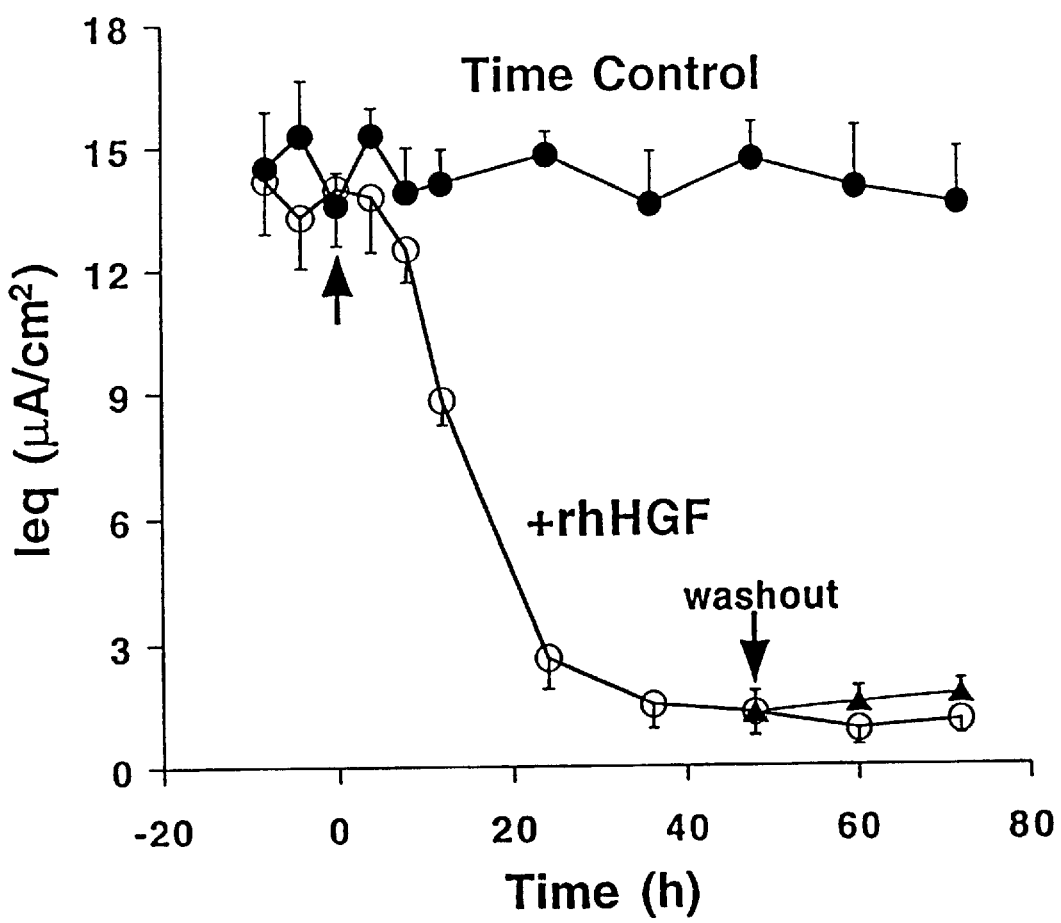
FIG. 2B is a graph illustrating the effect of rhuHGF (100 ng/ml) over the course of 72 hours on $I_{eq}$ of JME/CF 15 cells in vitro.
Figure 2C:
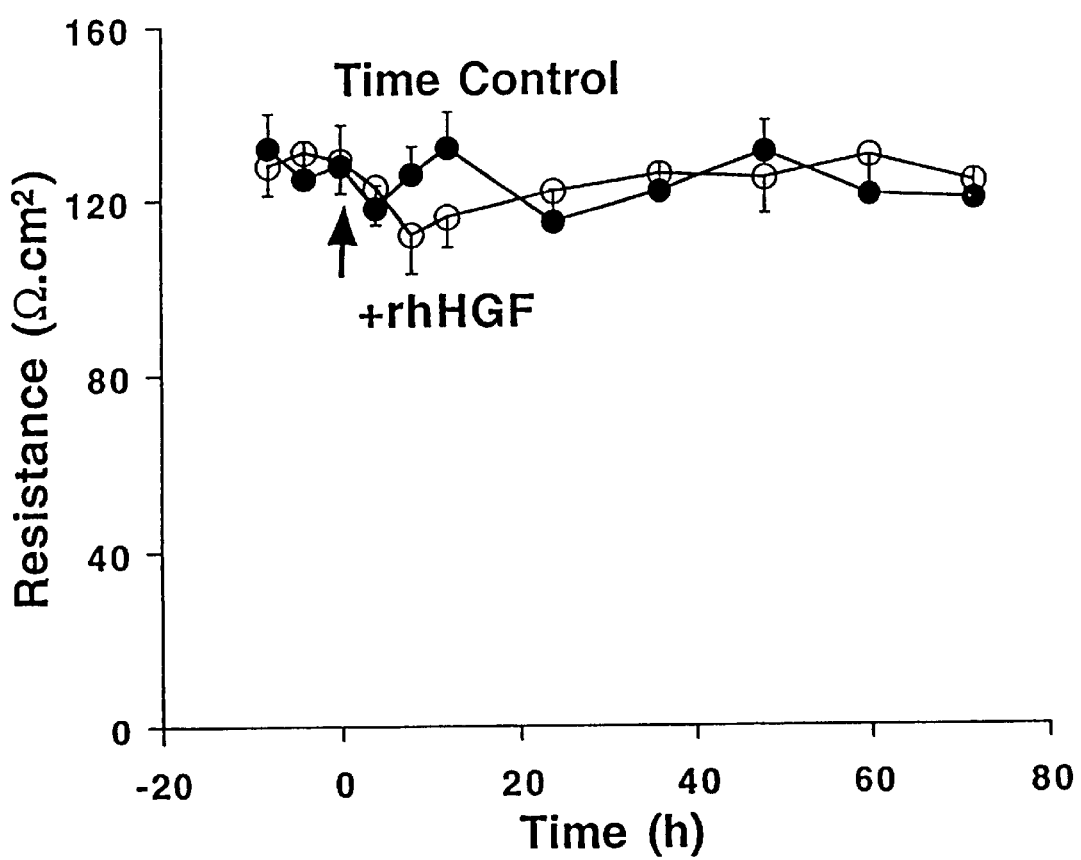
FIG. 2C is a graph illustrating the effect of rhuHGF (100 ng/ml) over the course of 72 hours on the transepithelial electrical resistance ($R_{te}$) of JME/CF 15 cell monolayers in vitro.

In a separate study, JME/CF 15 cell monolayers were cultured with 100 ng/ml rhuHGF (added basolaterally) for up to 72 hours. As shown in FIG. 2B, addition of rhuHGF to the basolateral medium decreased $I_{eq}$ with a $t_{1/2}$ of approximately 18 hours, and a maximal inhibition of approximately 90%. The values presented in FIG. 2B are means±SE, n=4. After 48 hours, 2 filters were continued to be exposed to the rhuHGF, while 2 filters were washed free of the rhuHGF. Washout of rhuHGF at 48 hours resulted in a partial recovery of $I_{eq}$ 24 hours later. (See FIG. 2B). $R_{te}$ values were not affected by rhuHGF treatment during this time course. (FIG. 2C).

Figure 2D:
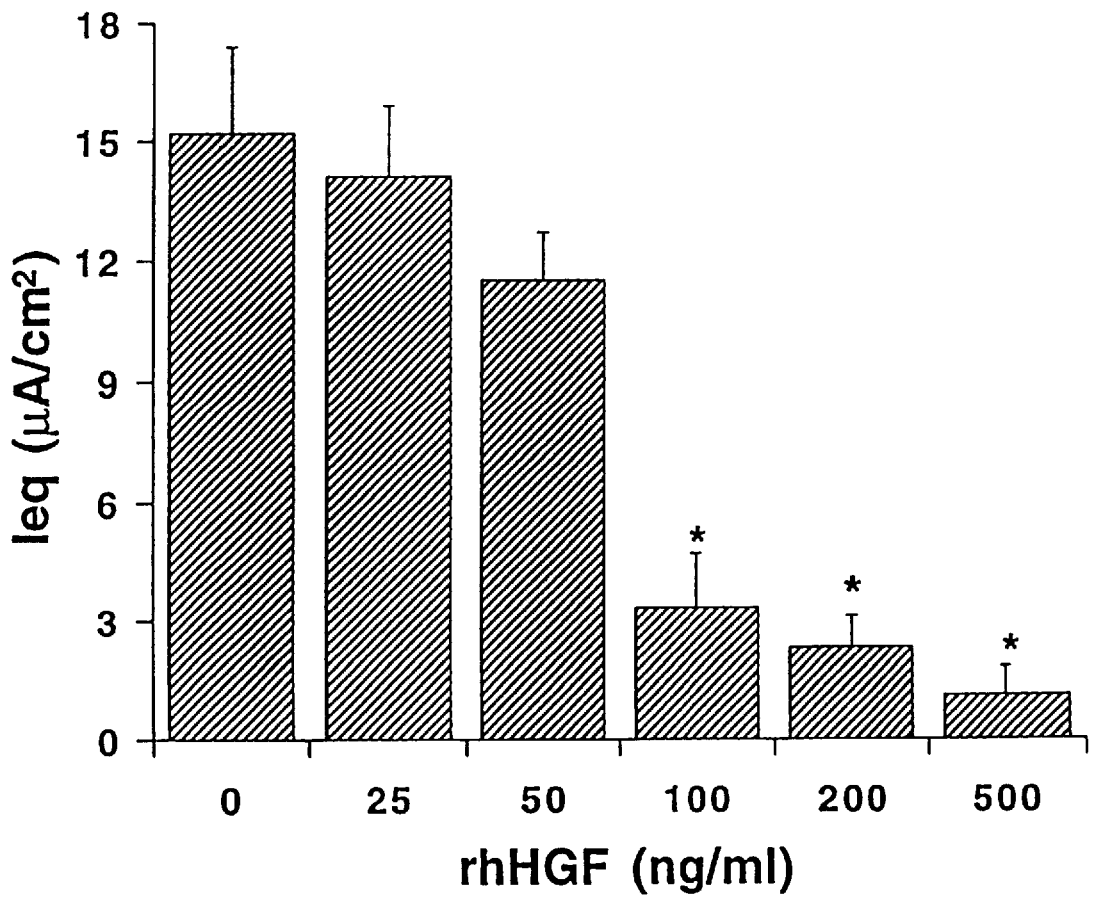
FIG. 2D is a graph illustrating the effect of varying doses of rhuHGF (0–500 ng/ml) on $I_{eq}$ of JME/CF 15 cells in vitro.

In a dose response experiment over this same time frame, confluent JME/CF 15 monolayers were cultured for 48 hours with varying doses of rhuHGF ranging from 0 to 500 ng/ml (added basolaterally). Baseline short circuit current measurements (mean±SEM, n=4) were compared using a paired student's t-test with p<0.05 being regarded as significant. As shown in FIG. 2D, 100 ng/ml rhuHGF appeared to result in near maximal response, although significant responses were observed at lower rhuHGF levels. ELISA evaluation [performed as described in Roos et al., Am. J. Physiol., 268:G380–G386 (1995)] of spent media from the cell monolayers demonstrated no detectable levels of rhuHGF were released from these cells and that approximately half of the rhuHGF spiked into media could be recovered after 48 hours of exposure (data not shown).

It is believed that the maximal effect on amiloride-sensitive $Na^+$ absorption will occur for approximately 48 hours with continuous rhuHGF exposure. It is believed that recovery of attenuated amiloride-sensitive $Na^+$ absorption will occur after approximately 12 hours following removal of rhuHGF.

Example 3

In an assay to determine the effect of rhuHGF on c-Met receptor phosphotyrosine content, JME/CF 15 cell monolayers were treated with 100 ng/ml rhuHGF (applied basolaterally or apically), lysed and evaluated for a c-Met associated phosphotyrosine content. The JME/CF 15 cell monolayers were lysed in 150 mM NaCl, 50 mM Tris-Cl, pH 8.0, 1% triton X-100, 0.1% SDS, 1% sodium deoxycholate and 1 mM phenylmethylsulfonyl fluoride and subjected to 8% SDS-PAGE. c-Met associated phosphotyrosine content was determined by immunoprecipitating with anti-Met COOH antibodies (Santa Cruz Biotechnology, Santa Cruz, Calif.) and blotting with anti-phosphotyrosine antibodies as described in U.S. Pat. No. 5,316,921. Control samples were treated identically but not exposed to rhuHGF.

Figure 3:
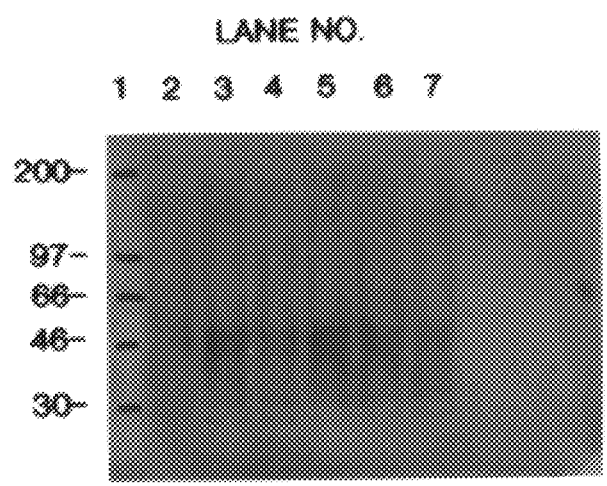
FIG. 3 shows a Western blot illustrating increased c-Met associated phosphotyrosine content of JME/CF 15 cells following exposure to 100 ng/ml rhuHGF.

FIG. 3 shows a Western blot of the following samples: molecular weight markers (Lane 1); an antibody control (Lane 2); a JME/CF 15 cell control (Lane 3); a JME/CF 15 cell sample treated basolaterally with rhuHGF for 7 days (Lane 4); a JME/CF 15 cell sample treated basolaterally with rhuHGF for 15 minutes (Lane 5); a JME/CF 15 cell control (Lane 6); a JME/CF 15 cell sample treated apically with rhuHGF for 15 minutes (Lane 7). It was found that the c-Met receptor is down-regulated following activation by HGF. Further, basolateral exposure of the cells to rhuHGF produced an increase in c-Met receptor phosphotyrosine content. Phosphorylation and down-regulation of c-Met preceded the decreases observed in ENaC expression and function.

Previous reports have suggested that the c-Met receptor is expressed only on the basolateral domain of polarized cells [Crepaldi et al., J. Cell. Biol., 125:313–320 (1994)]. No rhuHGF-induced actions were observed following presentation to only the apical surface of the cells and there is a rapid increase in phosphotyrosine of c-Met and a subsequent down-regulation of c-Met following the rhuHGF addition. These results are consistent with a receptor-mediated process.

Sodium channel protein level was also measured by Western blotting with a polyclonal antibody raised against the amiloride-sensitive epithelial $Na^+$ channel complex (ENaC) isolated from bovine kidney papillae [Sorscher et al., Am. J. Physiol., 255:C835–C843 (1988); Fuller et al., Am. J. Physiol., 269:C641–C654 (1995)]. Following 48 hour exposure to 100 ng/ml rhuHGF, JME/CF 15 cell monolayers were lysed in 150 mM NaCl, 50 mM Tris-Cl, pH 8.0, 1% triton X-100, 0.1% SDS, 1% sodium deoxycholate and 1 mM phenylmethylsulfonyl fluoride and subjected to 8% SDS-PAGE. Separated proteins were transferred onto a PVDF membrane, blocked with 5% non-fat dry milk, and incubated with 1.0 $\mu g/ml$ rabbit polyclonal antiamiloride sensitive $Na^+$ channel (ENaC) antiserum overnight. A goat anti-rabbit IgG horseradish peroxidase-conjugated secondary antibody was then added and an enhanced chemiluminescence kit (Amersham, Arlington Heights, Ill.) was used to detect the presence of ENaC. Antibody controls were performed the same except that no anti-ENaC antiserum was used.

Figure 4:
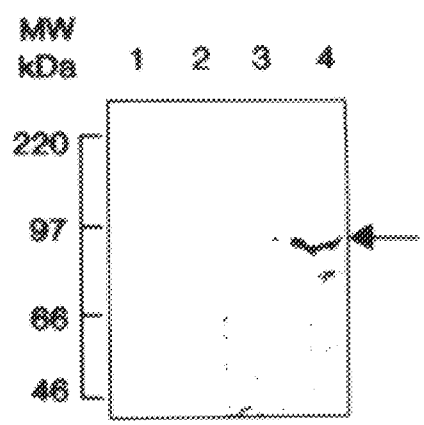
FIG. 4 shows a Western blot illustrating a reduction of the α-subunit of the amiloride-sensitive Na$^+$ channel protein content of JME/CF 15 cells following exposure to 100 ng/ml rhuHGF.

FIG. 4 shows a Western blot of the following samples: rhuHGF-treated cells, no antibody (Lane 1); control cells, no antibody (Lane 2); rhuHGF-treated cells with antibody (Lane 3); control cells with antibody (Lane 4). As shown in FIG. 4, levels of a specific 95–97 kDa protein in rhuHGF-treated cells was much lower than in control cells. The molecular weight of this protein is similar to that of the α-subunit of ENaC (approximately 95 kDa). Thus, it is believed that the rhuHGF may decrease the amiloride-sensitive sodium absorption in part (at least) by down regulating the expression of α-ENaC.

EXAMPLE 4

Primary bronchial epithelial cells from a human CF patient (designated R117H/deltaF508 genotype) were obtained by lung resection and cultured as described in Example 1. The cells were treated with 100 ng/ml rhuHGF (see Example 1). Before and after addition of the rhuHGF, the transepithelial resistance ($R_{te}$) and potential difference (PD) were monitored with the Millicell®-ERS meter, as described in Example 1.

Figure 5:
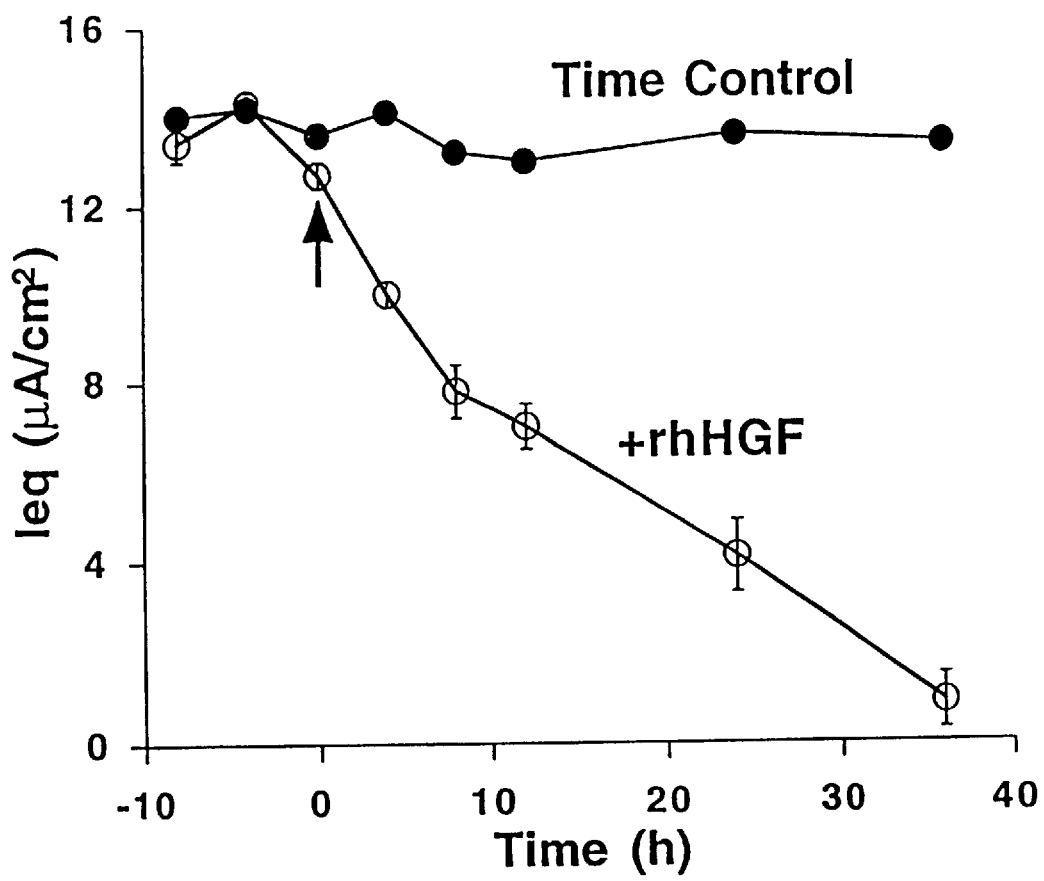
FIG. 5 is a graph illustrating the effect of 100 ng/ml rhuHGF over the course of 36 hours on $I_{eq}$ of primary bronchial epithelial cells obtained from a human cystic fibrosis patient and cultured in vitro.
Figure 6:
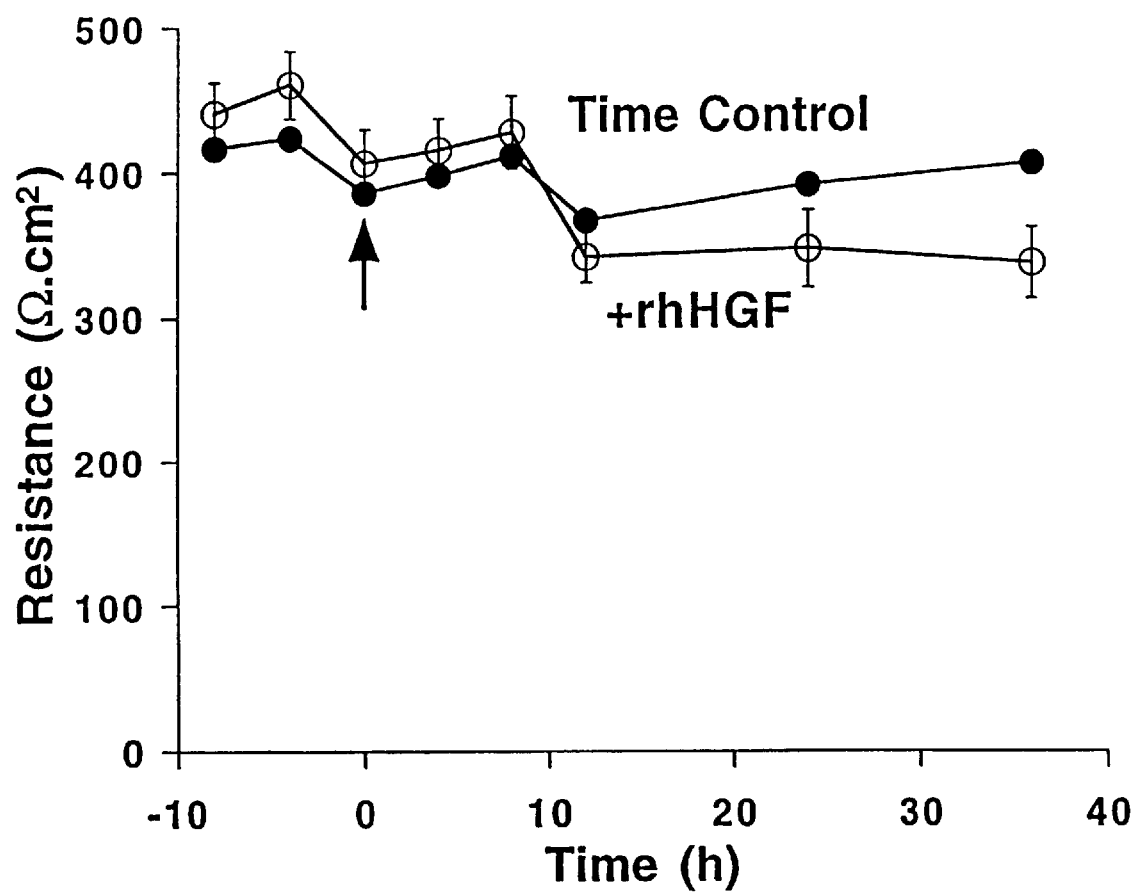
FIG. 6 is a graph illustrating the time course effect of 100 ng/ml rhuHGF on the transepithelial electrical resistance ($R_{te}$) of primary bronchial epithelial cells obtained from a human cystic fibrosis patient and cultured in vitro.

Treatment of the cells with the rhuHGF led to a decline in equivalent short circuit current ($I_{eq}$=PD/R) with a $t_{1/2}$ of approximately 10 hours, reaching values close to zero after approximately 36 hours. (FIG. 5). In contrast, matched time controls (receiving buffer alone) showed no changes of $I_{eq}$ over the same time period. (FIG. 5) The values presented in time controls in FIG. 5 (represented by closed circles) are an average from two different tissues and values presented for rhuHGF-treated monolayers (open circles) are means±SE, n=4. Transepithelial electrical resistance ($R_{te}$) was not affected by the rhuHGF treatment. (see FIG. 6).

Figure 7A:
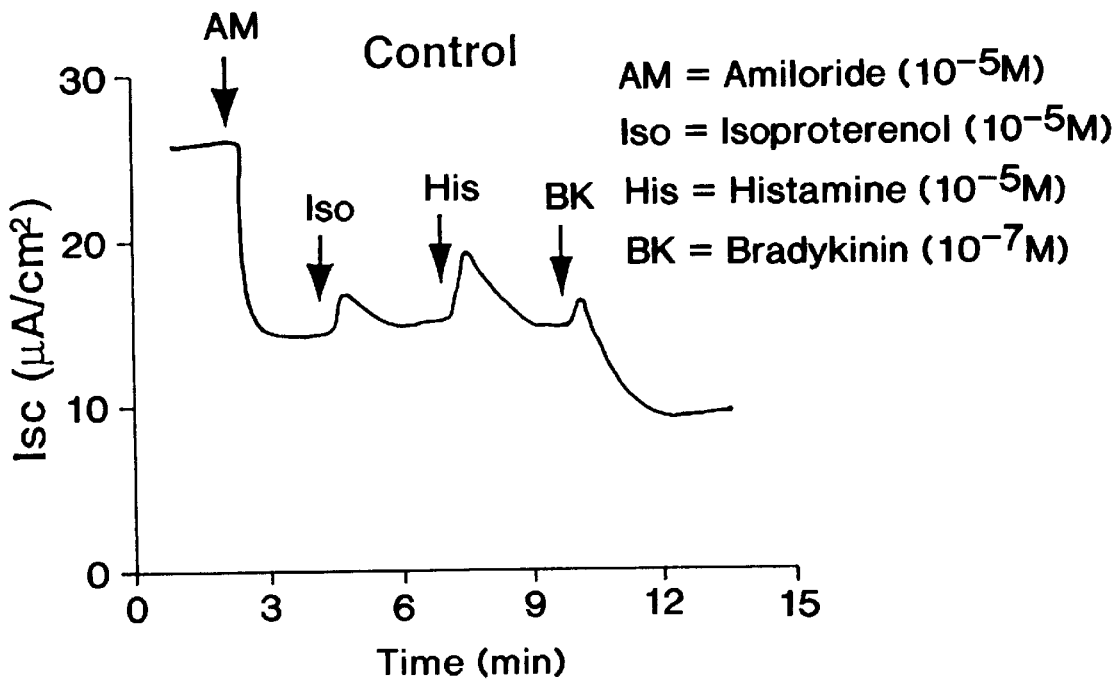
FIGS. 7A and 7B are graphs comparing the $I_{sc}$ responses of primary bronchial epithelial cells (obtained from a human cystic fibrosis patient and cultured in vitro) to challenge with amiloride, isoproterenol, histamine, and bradykinin following 48 hours exposure to 100 ng/ml rhuHGF.
Figure 7B:
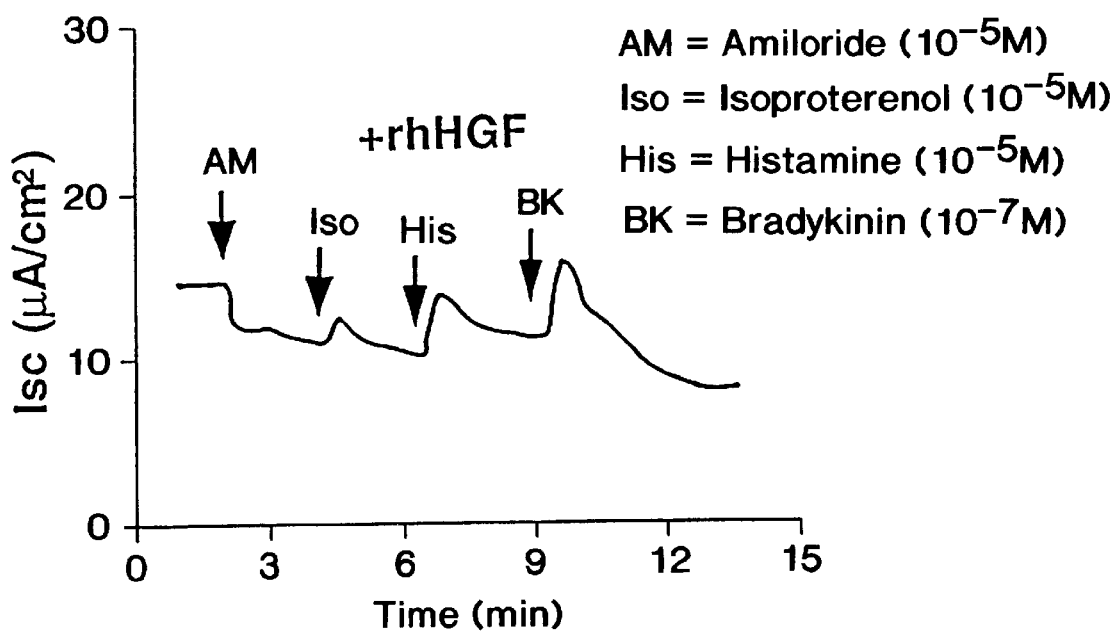

After 48 hours of culturing with rhuHGF, single control and HGF treated cells were tested in Ussing chambers, as described in Example 1. Transepithelial potential difference was clamped to zero by an external current passing circuit, and the resulting $I_{sc}$ was recorded continuously on a chart recorder. As shown in FIGS. 7A–7B, baseline $I_{sc}$ in the rhuHGF treated cells was lower than that of control (14 $\mu A/cm^2$ vs. 26 $\mu A/cm^2$).

The cells were also challenged with various secretagogues. The cells were challenged with apical additions of amiloride ($10^{-5}$M), followed by basolateral challenges with isoproterenol ($10^{-5}$M), histamine ($10^{-5}$M), and bradykinin ($10^{-7}$M). The control tissue was time-matched but received no rhuHGF treatment. The results are illustrated in FIGS. 7A–7B. Amiloride-sensitive sodium absorption in rhuHGF treated cells was dramatically lower than that of control cells (2 $\mu A/cm^2$ vs. 12 $\mu A/cm^2$). Treatment with rhuHGF did not significantly alter $R_{te}$ levels from pre-exposure values or time control tissues.

It was further found that rhuHGF was most effective when applied to the serosal side of these tissues. One tissue received 100 $\mu l$ of culture medium containing rhuHGF on its mucosal side, while a control tissue received 100 $\mu l$ of medium alone. In the treated tissue, pre-exposure values of $R_{te}$ and $I_{eq}$ were 415 ohm/$cm^2$ and 12.5 $\mu A/cm^2$; post exposure values were 585 ohm/$cm^2$ and 15.2 $\mu A/cm^2$. These values were similar to those observed for the control tissue values.

The data thus shows that HGF can diminish the abnormally high $Na^+$ absorption characteristic of CF-afflicted airway cells to levels comparable to non-CF cells. Although not fully understood, and not wishing to be bound by any particular theory, it is believed that the action of the HGF may result from a down regulation of the ENaC.

Various modifications of the invention in addition to those shown and described herein will become apparent to those skilled in the art from the foregoing description and fall within the scope of the appended claims.

What is claimed is:

1. A method of treating cystic fibrosis in a mammal, comprising administering an effective amount of hepatocyte growth factor ("HGF") to a mammal diagnosed as having cystic fibrosis.

2. The method of claim 1 wherein said HGF has at least 80% sequence identity with a native mammalian HGF.

3. The method of claim 2 wherein said HGF has at least 90% sequence identity with a native mammalian HGF.

4. The method of claim 3 wherein said HGF has at least 95% sequence identity with a native mammalian HGF.

5. The method of claim 4 wherein said HGF is human HGF.

6. A method of reducing sodium ion absorption in mammalian cells, comprising exposing said cells to an effective amount of HGF.

7. The method of claim 6 wherein said mammalian cells are afflicted with cystic fibrosis.

* * * * *